United States Patent [19]

McCaslin et al.

[11] Patent Number: 5,204,622
[45] Date of Patent: Apr. 20, 1993

[54] IMPROVED PROBE FOR INSPECTING TUBES HAVING MECHANISM FOR MAINTAINING ALIGNMENT OF PROBE AXIS OF ROTATION

[75] Inventors: Samuel C. McCaslin, Clairton; John J. Wilhelm, New Kensington, both of Pa.

[73] Assignee: Westinghouse Electric Corp., Pittsburgh, Pa.

[21] Appl. No.: 618,978

[22] Filed: Nov. 28, 1990

[51] Int. Cl.$^5$ .................. G01N 27/82; G01N 27/90; G21C 17/017
[52] U.S. Cl. .................. 324/220; 33/544.3; 324/262; 376/245
[58] Field of Search .................. 324/219–221, 324/262; 73/623; 33/544, 544.1, 544.2, 544.3, 544.4; 165/11.1, 11.2; 376/245, 249, 258

[56] References Cited

U.S. PATENT DOCUMENTS

| | | | |
|---|---|---|---|
| 2,992,390 | 7/1961 | De Witte . | |
| 3,225,294 | 12/1965 | McClung | 324/220 |
| 4,131,018 | 12/1978 | Muller et al. | 324/220 X |
| 4,139,822 | 2/1979 | Urich et al. | 324/219 |
| 4,153,875 | 5/1979 | Pigeon et al. | 324/220 |
| 4,189,944 | 2/1980 | Day et al. | 73/623 |
| 4,218,923 | 8/1980 | Triplett et al. | 73/623 |
| 4,304,134 | 12/1981 | Rouse et al. | 324/220 X |
| 4,372,161 | 2/1983 | de Buda et al. | 73/623 X |
| 4,460,920 | 7/1984 | Weber et al. | 73/623 X |
| 4,523,470 | 6/1985 | Muller et al. | 73/623 |
| 4,625,165 | 11/1986 | Rothstein | 324/220 |
| 4,633,177 | 12/1986 | David et al. | 324/220 |
| 4,797,613 | 1/1989 | Wentzell | 324/220 |
| 4,851,773 | 7/1989 | Rothstein | 324/220 |
| 4,937,524 | 6/1990 | Fasnacht et al. | 324/220 |
| 4,952,875 | 8/1990 | Adams et al. | 324/220 |

*Primary Examiner*—Gerard R. Strecker

[57] ABSTRACT

An improved tube inspection probe is provided of the type that includes a probe head assembly formed from a body member and a sensor holding mechanism for resiliently engaging a sensor against the inner wall of a tube, and a flexible cable connected to the body member for helically moving the probe head assembly through the interior of a tube. The improved probe comprises at least one centering device mounted around the cable for maintaining the axis of rotation of the cable in alignment with the center line of the tube, which includes a plurality of resilient finger members mounted around and extending away from the periphery of an annular member that surrounds the cable, wherein each of the fingers is canted at an acute angle with respect to a line tangent to the periphery of the annular member. The improvement may further comprise a button member resiliently mounted within the probe body in opposition to the resiliently-loaded sensor holding mechanism for maintaining the axis of the probe head assembly in alignment with the center line of the tube during operation, as well as a modular mount for detachably mounting the probe sensor to the sensor holding mechanism to facilitate the replacement or repair of the sensor.

28 Claims, 4 Drawing Sheets

IMPROVED PROBE FOR INSPECTING TUBES HAVING MECHANISM FOR MAINTAINING ALIGNMENT OF PROBE AXIS OF ROTATION

BACKGROUND OF THE INVENTION

This invention generally relates to probes for inspecting tubes, and is specifically concerned with a flexible eddy current probe capable of scanningly inspecting the interior wall of a heat exchanger tube in a nuclear steam generator.

Probes for inspecting the interior walls of heat exchanger tubes are known in the prior art. Such probes are particular useful in determining whether or not flaws such as cracks, pits, or localized areas of wall thinning are present in the heat exchanger tubes of operational nuclear steam generators. The ability of such probes to determine whether or not such flaws may be present is of paramount importance, as such flaws all constitute potential leak sites which could allow the radioactive primary side water which flows within these tubes to leak out into the non-radioactive, secondary water which surrounds these tubes and which is used to create the steam that drives the turbines in the plant. It is also important that the probe succeed in determining not only the presence of such a flaw, but also its location along the longitudinal axis of the tube so that a repair operation (such as a sleeving operation which creates an internal hydraulic "bridge" across the flawed section of the tube) may be performed in order to prevent radioactive water from the primary side of the generator from contaminating the secondary water in the generator. Finally, as the heat exchanger tubes in many steam generators are characterized by a bent portion in their center sections (called a "U-bend" in the art), it is further important the probe be flexible so that it can readily traverse and inspect the U-bend of the tube (which is, incidentally, one of the most common situses for tube flaws).

FIG. 1 illustrates one of the most advanced, state-of-the art probe designs for fulfilling all the aforementioned criteria.

One of the most advanced probes for inspecting such heat exchanger tubes generally comprises a probe head assembly that is connected to a flexible cable which is capable of both axially moving the head assembly to a desired location along the longitudinal axis of a heat exchanger tube, as well as rotating it so that a small "pancake-type" eddy current coil located on the side of the probe head assembly scanningly inspects the inner wall of the tube. To this end, the probe head assembly includes a generally egg-shaped body member, and a sensor holding mechanism for holding the eddy current probe and radially biasing it toward the inner wall of the tube. Such probes further include a pair of centering mechanisms which are disposed around the flexible cable that both enters into and exits from the body member of the probe head assembly which are adjacent to both the bottom and the top ends of the probe head assembly. The purpose of the centering mechanisms is to maintain the flexible cable in alignment with the center line of the tube when the cable is used to rotate the probe head assembly. To achieve this purpose, each of the centering mechanisms includes an annular member whose interior is fixedly engaged around the flexible cable, and whose exterior holds a plurality of radially disposed, monofilament fingers for bristles which sweepingly engage the inner walls of the tube when the probe is either moved axially or rotated within the tube.

While such probes are generally capable of achieving their intended purpose, the applicants have noted a number of drawbacks associated with this particular probe design. For example, the applicants have noted that the flexing of the bristles that radially extend out of the centering mechanisms can impart a jerky movement of the probe along the longitudinal axis of the heat exchanger being inspected. Such jerkiness in turn impairs the quality of the information received by the eddy current probe on the probe head assembly. Still another drawback associated with this design is the occasional failure of the probe head assembly to maintain its axis of rotation in alignment with the center line of the tube during a scanning operation. The resulting chattering of the head assembly against the inner walls of the tube further impairs the quality of the information received from the probe. A third drawback associated with this design is the fact that unwanted probe "lift-off" can occur when the probe head assembly is rotated throughout a section of the tube which has been rendered slightly ovalur by, for example, the mechanical process which create a U-bend in the center portion of such heat exchanger tubes. This is a particularly serious drawback, as the U-bend section of the tubes are more apt to have flaws as a result of the residual stresses created in these regions from the bending operations. The resulting probe lift-off can cause it either to fail to detect what serious flaws may be present, or to generate spurrous readings that indicate the presence of flaws that are in fact not there. Other shortcomings associated with this prior art probe include the fact that it is difficult, if not impossible to replace the delicate pancake-type eddy current probe if it should become damaged or fail. Also, this design allows the creation of a gap between the probe holding mechanism in the egg-shaped probe body which unfortunately is apt to catch the edges presented by the open ends of the heat exchanger tubes when the probe is being initially inserted into the tube.

Clearly, there is a need for a probe which retains all of the advantages associated with the previously described flexible probe, while eliminating all of the drawbacks.

SUMMARY OF THE INVENTION

Generally speaking, the invention is an improved probe for inspecting tubes which overcomes or at least ameliorates the aforementioned drawbacks associated with the prior art. More specifically, the invention is an improved probe of the type having a probe head assembly that includes a body member, a sensor holding mechanism for resiliently holding a sensor with respect to the body member, and a flexible cable for rotating the probe head assembly, where the improvement comprises at least one centering device that includes an annular member, and a plurality of resilient finger members mounted around and extending away from the periphery of the annular member such that each of the fingers is disposed in a plane that is orthogonal to the axis of rotation of the cable, and is also radially canted at an acute angle with respect to a line tangent to the portion of the periphery of the annular member that it extends away from. The radially canted orientation of the resilient fingers causes them to flex radially toward or away from the periphery of the annular member which secures them when the probe head assembly is pushed or pulled to a desired location along the longitudinal axis of a tube, which in turn eliminates the jerkiness associated with the centering devices used in connection with prior art probes caused by the flexing of such finger along the longitudinal axis of the probe. In the preferred embodiment, the acute angle that each of the resilient fingers is disposed at with respect to the periphery of the annular member is between about zero and 80 degrees, and even more preferably between about 30 and 60 degrees. Additionally, each of the resilient finger members is preferably canted at the same acute angle with respect to the periphery of the annular member.

To better maintain the axis of rotation of the probe head assembly in alignment with the center line of the tube during the operation of the probe, the improved probe may also include a button member resiliently mounted within the probe body in opposition to the sensor holding mechanism. The resiliently mounted button member applies a radially-oriented biasing force between the probe body and the inner wall of the tube which substantially cancels out the radially-oriented biasing force applied by the resiliently mounted sensor holding mechanism. In the preferred embodiment, a single spring means disposed within the probe body resiliently mounts both the sensor holding mechanism and the button member. The use of a single spring to achieve both functions not only advantageously simplifies the structure of the probe, but also assures that the radial biasing forces applied by the button member and the sensor holding mechanism will be identical.

To avoid the necessity of scrapping the entire probe when the eddy current sensor mounted within the probe, is need of repair, the improved probe may further include a modular mount for detachably mounting the sensor to the sensor holding mechanism. To avoid the probe sensor lift-off associated with the prior art, the sensor is secured to the modular mount through a rocking assembly that allows the sensor to pivot relative to the radius of the probe head assembly as it scanningly rotates within the tube. The ability of the sensor to pivot along the radius of the head assembly allows it to better follow the contour of off-round tubes and to avoid lifting-off. The modular mount may also include an electrical connector assembly, such as a pin and socket arrangement so that the sensor may conveniently be electrically connected and disconnected from the sensor holding mechanism.

Finally, the improved probe may also include at least one bumper member located between the sensor holding mechanism and the probe body for preventing the formation of a gap between the ends of the mechanism and the body that could catch an end of the tube being inspected.

BRIEF DESCRIPTION OF THE SEVERAL FIGURES

DETAILED DESCRIPTION OF THE PREFERRED EMBODIMENT

Figure 1A:
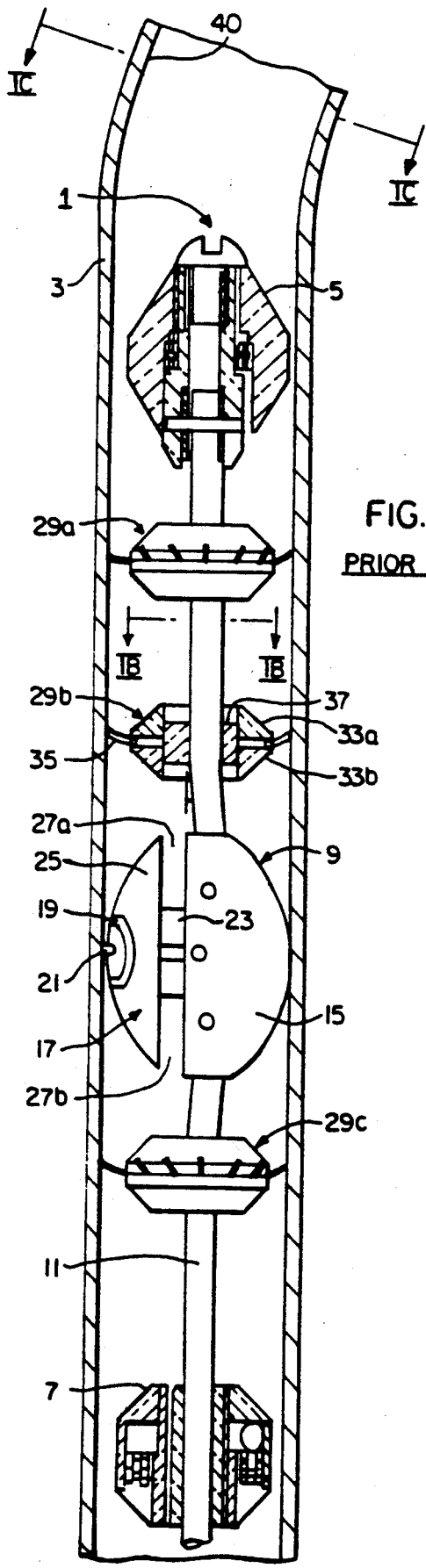
FIG. 1A is a partial cross-sectional side view of a prior art flexible probe which utilizes a pancake-type eddy current probe to scanningly inspect the inner walls of a heat exchanger tube.
Figure 1C:
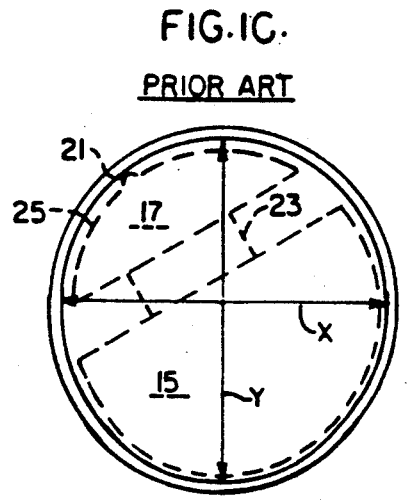
FIG. 1C is a cross-sectional view of an ovalur section of the heat exchanger tube illustrated in FIG. 1A along the line 1C—1C, illustrating how the tube ovalarity can result in unwanted lift-off of the eddy current probe.
Figure 1B:
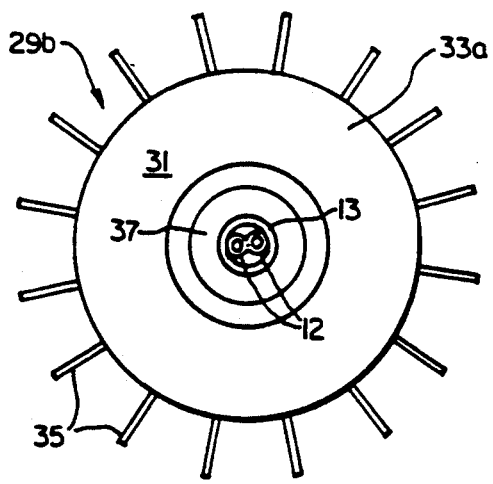
FIG. 1B is a plan view of one of the centering mechanisms used in the flexible probe illustrated in FIG. 1A along the line 1B—1B.

With reference now to FIGS. 1A, 1B and 1C, wherein like numerals designate like components throughout all the several figures, the invention is an improvement of a flexible prior art probe 1 that is capable of inspecting the inner walls of tubes 3 which may be the heat exchanger tubes of a nuclear steam generator. Such probes 1 generally comprise a beveled head piece assembly 5 for guiding the other probe components through the tube 3, a position coil assembly 7 for informing the system operator of the position of the probe 1 relative to a support plate (not shown) in a nuclear steam generator, and a probe head assembly 9 for carrying an inspection sensor that inspects the interior walls of the tube 3. The head piece assembly 5, the position coil assembly 7 and the probe head assembly 9 are all fixedly connected along a flexible cable 11 which is used both to move the probe 1 into a desired position along the longitudinal axis of the tube 3, as well as to rotate the probe head assembly 9 so that the eddy current sensor contained within the assembly 9 may scanningly inspect a selected section of the tube 3. It should be noted that the flexible cable 11 includes a plurality of electrical conductors 12 for powering both the eddy current coil and the position coil assembly 7, these conductors 12 being sealed within a cover 13 which not only serves to insulate the conductors 12, but also to efficiently transmit motion from the bottom of the cable 11 to each of the probe components.

The probe head assembly 9 generally comprises a body member 15 which is generally formed in the shape of a truncated, ovalur member, and a probe holding mechanism 17 which is slidably engaged to the body member 15 but yet which is resiliently and radially biased away from it by means of an internal spring (not shown). The purpose of the probe holding mechanism 17 is to hold a pancake-type eddy current coil 19 into resilient engagement against the inner walls of the tube 3 so that the coil 19 may scanningly inspect these walls 3 when the probe head assembly 9 is helically moved within the tube 3. A ferrite core 21 is positioned in the center of the eddy current coil 19 in order to focus the magnetic field generated by the coil 19. As may best be appreciated with reference to both FIGS. 1A and 1C, the probe holding mechanism 17 includes a tubular portion 23 which is slidably engaged and spring loaded within a bore (not shown) present in the body member 15, as well as a head portion 25 which supports the eddy current coil 19. It should be noted that the design of the prior art probe 1 allows the creation of air gaps 27a,b between the head portion 25 of the probe holding mechanism 17, and the body member 15 of the probe head assembly 9.

To help to maintain the flexible cable 11 in alignment of the center line of the tube 3 when the cable 11 is used to rotate the probe head assembly 9, prior art probe 1 further includes three centering devices 29a,b,c located both above and beneath the probe head assembly 9. Each of these centering devices 29a,b,c includes an annular assembly 31 formed from a pair of retaining ring members 33a,b which serve to mount a plurality of resilient finger members 35 formed from monofilament bristles in the radial orientation best seen in FIG. 1B. A mounting ring 37 disposed around the inner opening of the two retaining ring members 33a,b fixedly mounts each of the centering devices 29a,b,c around the flexible cable 11. In operation, the resilient finger members 35 of each of the centering devices 29a,b,c sweepingly engages the inner walls of the heat exchanger walls 3 as the probe 1 is moved axially or rotated within this tube in order to maintain the cable 11 (and hence the axis of rotation of the other components of the probe 1) into alignment with the center line of the tube 3.

As has been indicated earlier, while the prior art probe 1 illustrated in FIGS. 1A, B and C is generally capable of performing its intended function, it also suffers from several drawbacks. For example, the applicants have noted that the axially-oriented flexing of the monofilament finger members 35 of the centering devices 29a,b,c can cause the entire probe 1 to move in a relatively jerky fashion when it is pulled or pushed along the longitudinal axis of the tube 3, due to the tendency of these fingers members 35 to want to "pole vault" whenever the system operator wishes to change the axial direction of movement of the probe 1 within the tube 3. The resulting jerky motion degrades the value of the information received from the eddy current coil 19 as it scanningly inspects the interior wall of the tube 3. Still another drawback associated with this prior art probe 1 is the tendency of the eddy current coil 19 to lift off of the inner wall of the tube when the probe head assembly 9 is rotated within a section of the tube that has been deformed so that it possesses a slightly ovalur cross section. This phenomenon is best appreciated with respect to FIGS. 1A and 1C. FIG. 1A illustrates how the heat exchanger tube 3 looks as it leads into a U-bend. The mechanical processes used to create such U-bends in heat exchanger tubes 3 creates a slight ovularity in the shape of the tube, best seen with respect to FIG. 1C. Specifically, the inner diameter of the heat exchanger tube 3 along the x axis is noticeably shorter than the inner, diameter of this tube 3 along the y axis. The applicants have observed when the probe head assembly 9 of the prior art probe 1 is rotated within such an ovalur section of the heat exchanger tube 3, the spring which normally biases the eddy current coil 19 into wiping engagement against the inner wall of the tube 3 fails to maintain this coil 19 into such engagement when the inner shape of the tube is ovalur. The resulting lift-off results in spurious readings which can result either in the failure to locate a flaw in the U-bend region of the tube 3, or a reading of a flaw which in fact is not present. Other drawbacks associated with prior art probe 1 include the fact that the air gaps 27a,b can catch the open ends of the tube 3 during the initial insertion of the probe 1, and that the eddy current coil 19 cannot easily be removed from the probe holding mechanism 17 when the coil 19 breaks or otherwise becomes defective, which in turn results in the scrapping of the entire probe 1. A final shortcoming of the prior art probe 1 is the fact that the spring loaded probe holding mechanism 17 does not always serve to maintain the axis of rotation of the probe head assembly 9 in alignment with the center line of the tube 3 during an inspection operation. The resulting axial misalignment can again cause the probe head assembly 9 to "chatter" against the tube walls 3, which again degrades the value of the information received from the eddy current coil 19.

Figure 2:
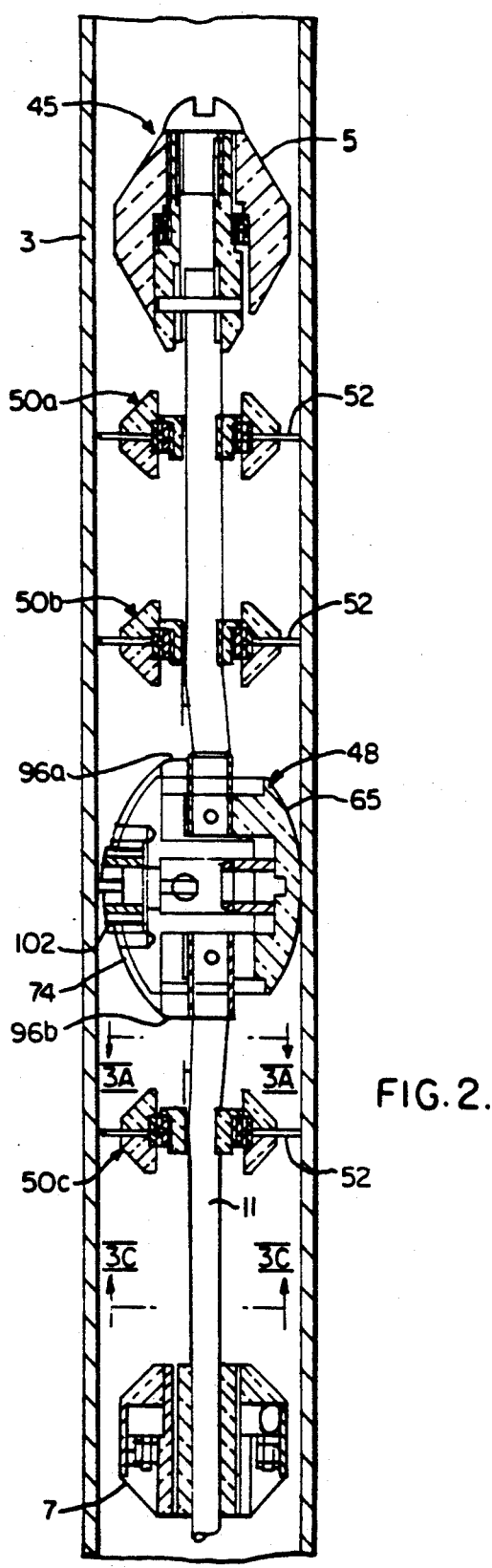
FIG. 2 is a cross-sectional side view of the improved probe of the invention.
Figure 3A:
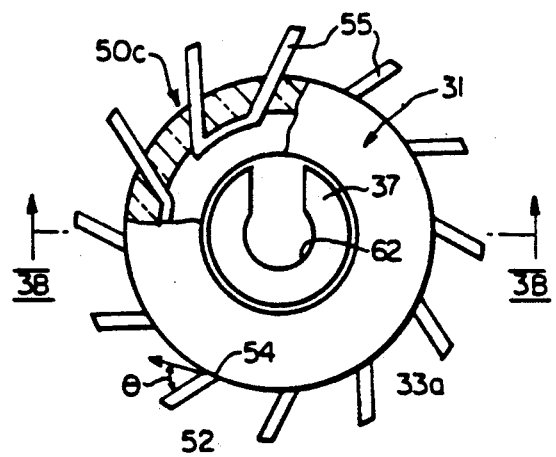
FIG. 3A is a plane view of one of the centering mechanisms used in the improved probe along the line 3A—3A.
Figure 3B:
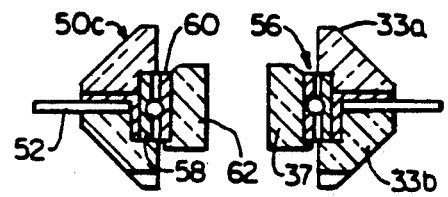
FIG. 3B is a cross-sectional side view of the improved centering mechanism illustrated in FIG. 3A along the line 3B—3B.
Figure 3C:
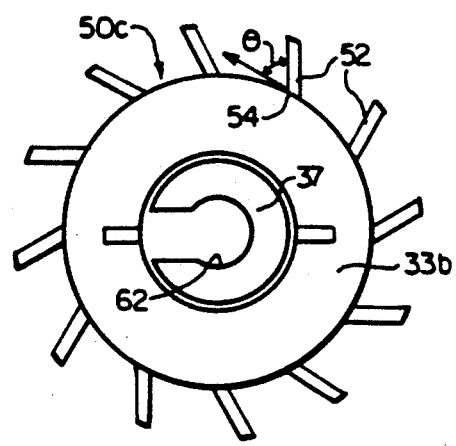
FIG. 3C is a bottom view of the centering mechanism illustrated in FIG. 2 along the line 3C—3C.

FIG. 2 illustrates the improved probe 45 of the invention, which includes the head piece assembly 5, the position coil assembly 7 and the flexible cable 11 that were present in the prior art probe 1, but which further includes an improved probe head assembly 48 which eliminates the shortcomings associated with the probe head assembly 9 of the prior art probe 1, as well as improved centering devices 50a,b,c which allow the probe 45 to be pushed or pulled along the longitudinal axis of the tube 3 smoothly.

With reference now both to FIG. 2 and FIGS. 3A, 3B and 3C, each of the improved centering devices 50a,b,c achieve their function of centering the probe 45 while allowing smooth axial movement thereof by means of a plurality of resilient mounting fingers 52 which are canted relative to the periphery of the annular assembly 31, rather than being radially oriented with respect to the annular assembly 31. More specifically, each of the resilient finger members 52 is canted at an acute angle with respect to the portion 54 of the periphery of the annular assembly 31 from which it extends. While this acute angle (designated by the Greek letter theta in FIGS. 3A and 3C) may be anywhere between 0° and 80°, this angle is preferably between about 30 and 60' in the preferred embodiment. Additionally, as is most evident with respect to FIG. 3B, all of the resilient mounting fingers 52 are preferably disposed in a plane with is orthogonal to the axis of rotation of the cable 11. The provision of canted resilient finger members 52 arranged in such a plane insures that these finger members 52 can and will deflect only in a direction orthogonal with respect to the axis of rotation of the cable 11 as the probe 45 is pushed or pulled into a different axial location within the tube 3, thereby eliminating the jerkiness of such axial movement associated with the aforementioned "pole-vaulting" of the finger member present in the prior art centering devices 29a,b,c. To insure that the distal ends of each of the finger members 52 will not "dig" or catch on the inner walls of the tube 3, it should be noted that the distal ends 55 are cut at an angle so that they engage the inner walls of the tube 3 with a substantially flat surface, as opposed to a pointed surface. Finally, to eliminate any chance of the "pinwheel" orientation of the finger members 55 applying a spurious torque to the cable 11 is the finger member 55 as moved axially along the inner walls of the tube 3, a bearing 56 is provided between the retaining ring members 33a,b which serve to hold the finger members 55 in place, and the mounting ring 37 which serves to secure each of the centering devices 55a,b,c to the flexible cable 11. As is most evident in FIG. 3B the outer race 58 of the bearing 56 is secured onto the inner diameter of the annular retaining ring members 33, while the inner race 60 of this bearing 56 is secured around the outer periphery of the mounting ring 37.

With reference now to FIGS. 4, 5A, 5B and 5C, the improved probe head assembly 48 of the probe 45 of the invention includes a body member 65 which is shaped like a truncated ovalur solid that has a pair of opposing cable mounting recesses 66a,b at either end. As is best seen with respect to FIG. 4, one end of two of the segments which form the flexible cable 11 is secured into each of the cable mounting recesses 66a,b by means of rivets 68. A radially oriented octagonal recess 70 with radiused corners is disposed in the middle portion of the body member 65 between the cable mounting recesses 66a,b. This octagonal recess 70 includes the tubular portion 72 of a probe holding mechanism 74 whose ultimate purpose is to support an eddy current coil in scanning engagement against the inner wall of the tube 3. As is best seen with respect to FIG. 5A, the tubular portion 72 of the probe holding mechanism 74 is likewise octagonally shaped to allow slidable movement between the tubular portion 72 and the square recess 70 and the body member 65, but to prevent rotational motion from occurring between these two components.

Figure 4:
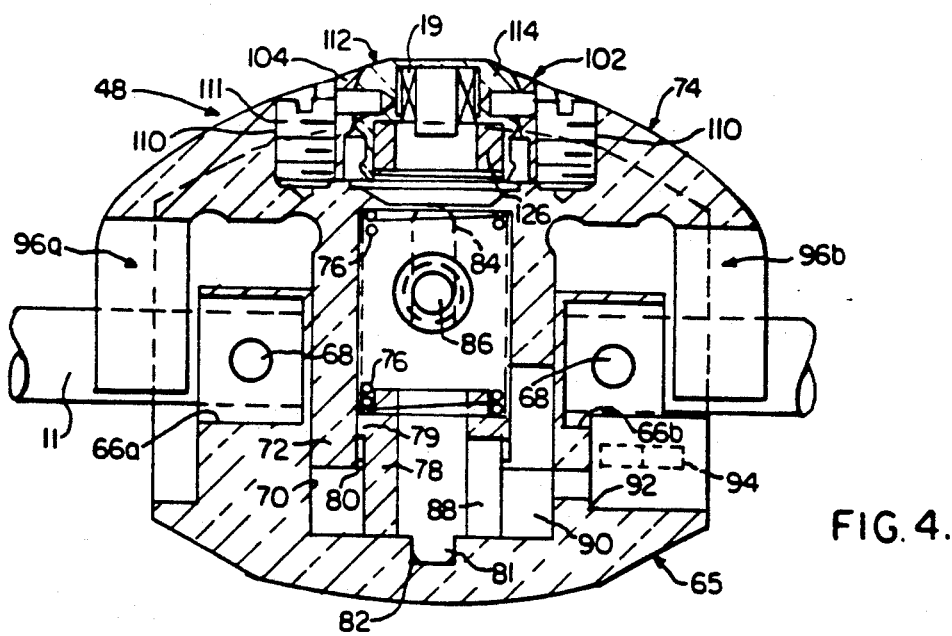
FIG. 4 is a cross-sectional side view of the probe head assembly used in the improved probe of the invention.
Figure 5A:
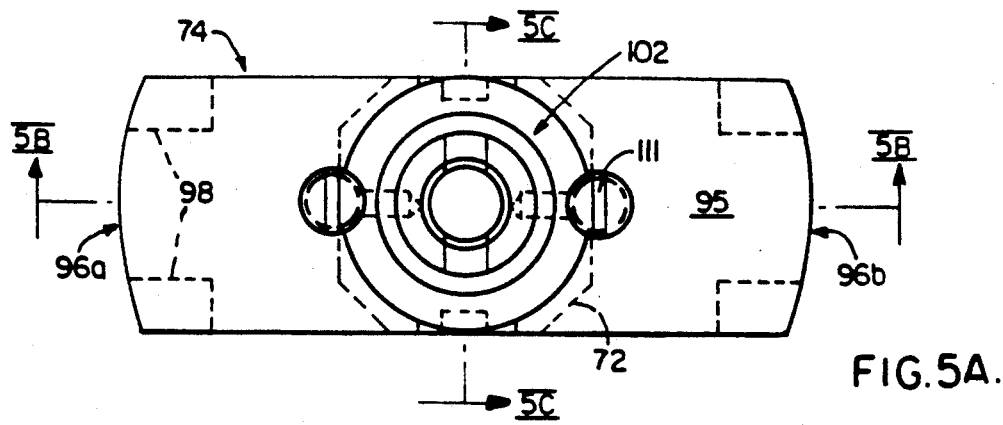
FIG. 5A is a plane view of the probe holding mechanism used in the probe head assembly illustrated in FIG. 4.
Figure 5B:
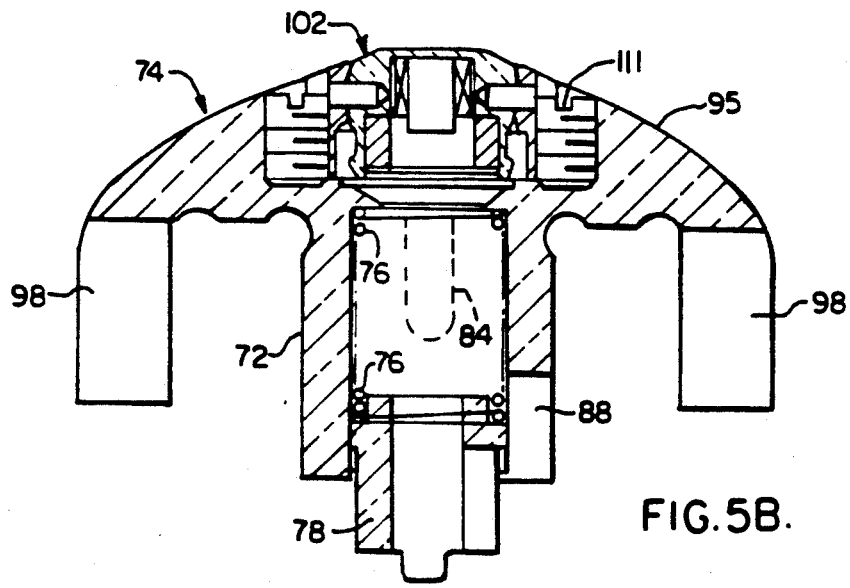
FIG. 5B is a cross-sectional side view of the probe holding mechanism illustrated in FIG. 5A along the lines 5B—5B.
Figure 5C:
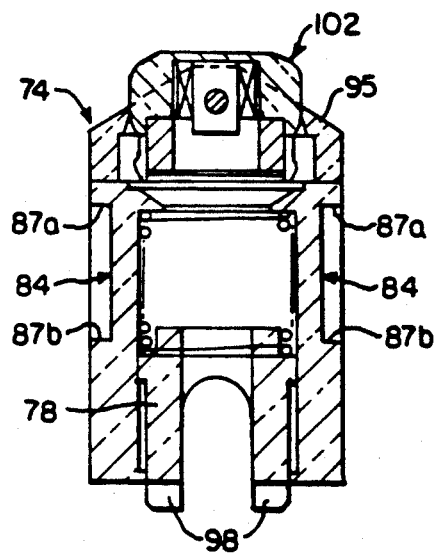
FIG. 5C is a cross-sectional end view of the probe holding mechanism illustrated in FIG. 5A along the lines 5C—5C.

In its interior, the tubular portion 72 of the probe holding mechanism 74 includes a spring 76 for biasing the probe holding mechanism 74 away from the body member 65. This spring 76 reacts against and is retained by a spring retainer 78 easily seen in both FIGS. 4 and 5B. The spring retainer is in turn secured within the hollow interior of the tubular portion 72 by means of an annular shoulder 79 integrally formed around its upper end which is captured by an annular lip 80 that circumscribes the inner diameter of the tubular portion 72 at its bottom end. Unless noted otherwise, all of the components forming the probe head assembly 65 are formed from a resilient plastic material such as Delrin ® which allows components such as the spring retainer 78 to be "snap-fitted" into the position illustrated in FIG. 4 due to the resiliency of the material forming the capturing lip 80. The bottom end of the spring retainer 78 is provided with a lug 81 which, as is evident in FIG. 4, is receivable within a complimentarily shaped recess 82 present within the body member 65. With reference in particular to FIGS. 4 and 5C, the probe holding mechanism 74 is retained within the body member 65 by the inner action of a pair of opposing set screws 86 which are secured within threaded bores present in the sides of the body member 65 and whose distal ends are receivable within longitudinal recesses 84. During the assembly of the improved probe head assembly 48, these set screws 86 are screwed into engagement with the lateral walls of the recesses 84, and then screwed back slightly to eliminate frictional engagement between the distal ends of the screws 86, and the lateral walls of the recesses 84. Thus assembled, the reciprocating movement of the probe holding mechanism 74 is confined by the action of the distal ends of these screws 86, and the upper and lower edges 87a,b of the recesses 84, which act as stops.

Near the bottom end of the tubular portion 72 of the probe holding mechanism 74 is a bore 88 which, along with a registering passageway 90 located in the body member 65 forms a pathway for the electrical conductors 12 present in the flexible cable 11 to be connected to leads (not shown) which extend down from the eddy current coil 19. To facilitate the electrical connection and disconnection of the eddy current coil leads from the electrical conductors 12 present in the flexible cable 11, the body member 65 further includes a connector cavity 92 into which a socket assembly 94 may be located.

To prevent the formation of the previously described, tube-catching air gaps 27a,b present in the prior art probe 1, the head portion 95 of the probe holding mechanism 74 is provided with bumper members 96a,b on each of its ends. As is best seen with reference to FIG. 5C, each of these bumper members 96a,b includes a pair of prongs 98 which define a slot 100 into which the cable 11 may be slidably received in conformance with the radial movement of the probe holding mechanism 74 relative to the body member 65 as the probe 45 is rotated within the tube 3.

Figure 6:
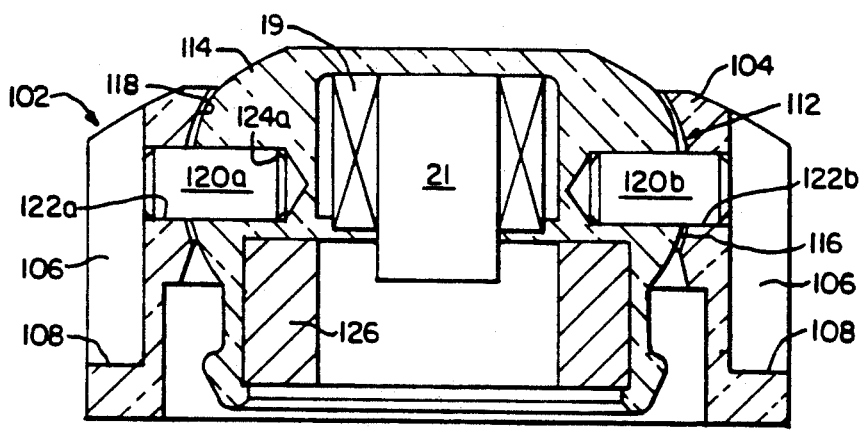
FIG. 6 is a cross-sectional side view of the modular mount used to detachably mount the eddy current coil to the probe holding mechanism.

With reference now to FIG. 6, the probe holding mechanism 74 of the improved probe head assembly 48 of the invention includes a modular coil mount 102 which detachably mounts the eddy current coil 19 to the mechanism 74. Such detachable mounting is highly desirable as it allows the eddy current coil 19 to be easily replaced in the event of failure, thereby obviating the need to scrap the entire probe 45. To this end, the modular coil mount 102 includes a retainer member 104 which is detachably connectable to the probe holding mechanism 74 by virtue of a pair of opposing recesses 106 which terminate in ledges 108 near the bottom of the mount 102. These recesses 106 and ledges 108 are alignable with a pair of opposing partial bores 110 present at the top of the head portion 95 of the probe holding mechanism 74 such that the recesses 106 and partial bores 110 form a complete, screw-receiving bore when the retainer member 104 is placed into the position illustrated in FIG. 4. A pair of mounting screws 111 which are threadedly engagable with the partial bores 110 bear against the ledges 108 when the coil mount 102 is secured into the mounted position illustrated in FIG. 4. To avoid unwanted lift-off from occurring between the eddy current coil 19 and the inner wall of the heat exchanger tube 3, the coil 19 is held by a rocking assembly 112 which is pivotally movable within the retainer member 104. The rocking assembly 112 includes a rocking member 114 having a partial, spherical exterior 116 which fits within a partial spherical interior 118 that defines the inner diameter of the retainer member 104. A pair of pivot pins 120a,b insertable through mutually registering bores 122a,b and 124a,b present in the retainer member 104 and the rocking member 112, respectively, pivotally mount the rocking member 114 to the retainer member 104. It should be noted that an annular magnet 126 is disposed within the rocking member 114 immediately below both the coil 19 and ferrite core 21 of the eddy current probe. The magnet 126 coacts with the ferrite core 21 to focus the lines of magnetic flux emanated by the eddy current coil 19. In operation, the ability of the rocking member 114 to pivot relative to the retainer member 104 results in a smooth ride for the eddy current coil 19 over portions of the inner walls of the tube 3 which are not perfectly circular, as is the case with the ovalur cross sections of the tube 3 associated with the previously described U-bend portions 40, and as is further the case with tubes that have been dented as a result of the accumulation of deposits in the annular spaces between the heat exchanger tubes and the openings (not shown) in the support plates which laterally hold them within a steam generator.

Figure 7:
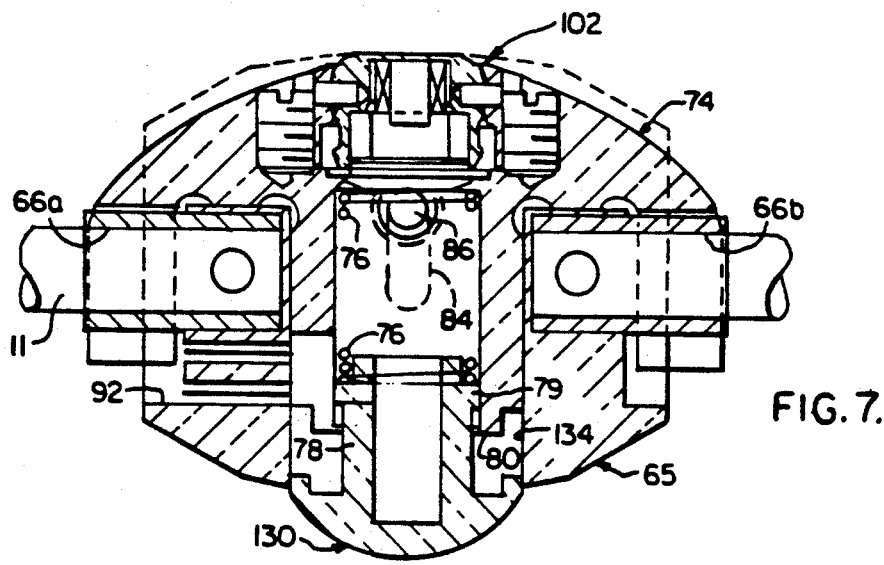
FIG. 7 is a cross-sectional side view of a second preferred embodiment of the probe head assembly used in the invention.

FIG. 7 illustrates a second preferred embodiment of the invention which advantageously includes the additional feature of a resilient button 130 disposed in opposition to the modular coil mount 102 of the probe head assembly 65. As is evident from FIG. 7, the resilient button 130 is formed from a rounded head piece 132 that projects down from the bottom portion of the previously described spring retainer 78. The rounded head 132 of this button 130 projects through a through hole 134 formed by extending the previously described square recess 70 in the body member 65. The fact that the resilient button is formed from an extension of the previously described spring retainer 78 advantageously allows the use of a single spring 76 to spring load both the probe holding mechanism 74 with respect to the body member 65, as well as the resilient button 130 with respect to the body member 65. Again, both the probe holding mechanism 74 and the resilient button 130 are secured in place within the body member 65 by means of the previously described set screws 86 whose distal ends are slidably received within slots 84.

In operation, the radially-oriented biasing force applied by the resilient button 130 against the inner walls of the heat exchanger walls 3 coacts with the resilient, radially oriented biasing force that the probe holding mechanism 74 applies against these tube walls to help to positively maintain the axis of rotation of the probe head assembly 65 into alignment with the center line of the tube, thereby helping to increase the accuracy and reliability of the information transmitted by the eddy current coil 19.

We claim:

1. An improved probe of the type having a probe head assembly that includes a sensor, and a flexible cable connected to said assembly for rotating said assembly within a tube such that said sensor scanningly inspects the inner walls of said tube, wherein the improvement comprises a centering device including an annular member mounted around said cable in the vicinity of said probe head assembly for maintaining the axis of rotation of said cable in alignment with the center line of said tube, said member including a plurality of resilient finger members mounted around and extending away from the periphery of said annular member for engaging the inner walls of said tube and applying a centering force to said cable through said member, wherein each of said fingers is disposed in a plane that is orthogonal to the axis of rotation of said cable, but which is canted at an acute angle with respect to a line tangent to the portion of said periphery of the annular member that it extends away from.

2. An improved probe as defined in claim 1, wherein said acute angle is between about 0° and 80°.

3. An improved probe as defined in claim 1, wherein all of said resilient finger members are disposed in the same plane.

4. An improved probe as defined in claim 1, wherein said annular member is rotatably mounted around said cable through a bearing means.

5. An improved probe as defined in claim 1, wherein each of said resilient finger members is canted at the same acute angle.

6. An improved probe as defined in claim 1, wherein said probe head assembly is of the type that includes a body member, and a sensor holding mechanism for resiliently holding said sensor with respect to said body member such that said sensor wipingly engages the inner walls of said tube when the head assembly is rotated, wherein said improvement further comprises modular means for detachably mounting said sensor to said holding mechanism to facilitate replacing said sensor.

7. An improved probe as defined in claim 6, wherein said sensor includes at least one cable for receiving electrical power, and said modular means further includes means for electrically connecting said cable to a source of power in said probe body member.

8. An improved probe as defined in claim 1, wherein said probe head assembly is of the type that includes a body member, an a sensor holding mechanism for resiliently holding said sensor with respect to said body member such that said sensor wipingly engages the inner walls of said tube when the head assembly is rotated and a gap is formed between the ends of said body member and said sensor holding mechanism, wherein the improvement further comprises at least one bumper member mounted onto said probe head assembly for covering said gap between the ends of said mechanism and said body member to prevent said gap from catching an end of the tube being inspected.

9. An improved probe as defined in claim 1, wherein said probe head assembly is of the type that includes a body member, and a sensor holding mechanism for resiliently holding said sensor with respect to said body member such that said sensor wipingly engages the inner walls of said tube when the head assembly is rotated, wherein said improvement further comprises a button member resiliently mounted within said probe body member opposite from said sensor holding mechanism for maintaining the axis of rotation of said probe head assembly in alignment with the center line of said tube.

10. An improved probe as defined in claim 9, wherein sad improvement further comprises a single spring means disposed within said probe body member for resiliently mounting both said sensor holding mechanism and said button member.

11. An improved probe for inspecting tubes of the type having a rotatable probe head assembly that includes a body member, and a sensor holding mechanism for resiliently holding a sensor with respect to said body member such that said sensor wipingly engages the inner walls of said tube when the head assembly is rotated, wherein the improvement comprises a button member resiliently mounted within and reciprocally movable with respect to said probe body member opposite to said sensor holding mechanism for maintaining the axis of rotation of said probe head assembly in alignment with the center line of said tube.

12. An improved probe as defined in claim 11, wherein said improvement further comprises a single spring means disposed within said probe body member for resiliently mounting both said sensor holding mechanism and said button member.

13. An improved probe as defined in claim 11, wherein said probe is further of the type that includes a flexible cable connected to said probe head assembly for rotating said assembly, and wherein said improvement further comprises a centering device including an annular member mounted around said cable in the vicinity of said probe head assembly for maintaining the axis of rotation of said cable in alignment with the center line of said tube, said member including a plurality of resilient finger members mounted around and extending away form the periphery of said annular members for engaging the inner walls of said tube and applying a centering force to said cable through said member, wherein each of said fingers is disposed in a plane that is orthogonal to the axis of rotation of said cable, but which is canted at an acute angle with respect to a line tangent to the portion to said periphery of the annular member that it extends away from.

14. An improved probe as defined in claim 13, wherein said acute angle is between about 0° and 80°.

15. An improved probe as defined in claim 13, wherein said acute angle is between about 30° and 60°.

16. An improved probe as defined in claim 13, wherein said annular member is rotatably mounted around said cable through a bearing means.

17. An improved probe as defined in claim 16, wherein the improvement further comprises a bearing means disposed between said cable and the inner diameter of said annular member.

18. An improved probe as defined in claim 11, wherein the improvement further comprises modular means for detachably mounting said sensor to said holding mechanism to facilitate replacing said sensor.

19. An improved probe as defined in claim 11, wherein said sensor includes at least one cable for receiving electrical power, and said modular means further includes means for electrically connecting said cable to a source of power in said probe body member.

20. An improved probe as defined in claim 11, wherein said probe is of the type where a gap is formed between the ends of said body member and said sensor holding mechanism, and wherein bumper member mounted on said probe head assembly for covering said gap between the ends of said mechanism and said body member to prevent said gap from catching an end of a tube being inspected.

21. An improved probe for inspecting tubes of the type having a rotatable probe head assembly that includes a body member, and a sensor holding mechanism for resiliently holding a sensor with respect to said body member such that said sensor wipingly engages the inner walls of said tube when the head assembly is rotated, wherein the improvement comprises a modular means for detachably mounting said sensor to said holding mechanism to facilitate replacing said sensor, and wherein said probe head assembly is of the type that includes a body member, and a sensor holding mechanism for resiliently holding said sensor with respect to said body member such that said sensor wipingly engages the inner walls of said tube when the head assembly is rotated, wherein said improvement further comprises a button member resiliently mounted within and reciprocally movable with respect to said probe body member opposite from said sensor holding mechanism for maintaining the axis of rotation of said probe head assembly in alignment with the center line of said tube.

22. An improved probe as defined in claim 21, wherein said improvement further comprises a single spring means disposed within said probe body for resiliently mounting both said sensor holding mechanism and said button member.

23. An improved probe as defined in claim 21, wherein the improvement further comprises a centering device including an annular member mounted around said cable in the vicinity of said probe head assembly for maintaining the axis of rotation to said cable in alignment with the center line of said tube, said member including a plurality of resilient finger members mounted around and extending away form the periphery of said annular member for engaging the inner walls of said tube and applying a centering force to said cable through said member, wherein each of said fingers is disposed in a plane that is orthogonal to the axis of rotation of said cable, but which is canted at an acute angle with respect to a line tangent to the portion of said periphery of the annular member that it extends away from.

24. An improved probe as defined in claim 23, wherein said acute angle is between about 0° and 80°.

25. An improved probe as defined in claim 23, wherein said acute angle is between about 30° and 60°.

26. An improved probe as defined in claim 23, wherein each of said resilient finger members is canted at the same acute angle.

27. An improved probe as defined in claim 21, wherein said probe is of the type where a gap is present between the ends of the probe body member and the sensor holding mechanism, and wherein the improvement further comprises at least one bumper member mounted onto said probe head assembly for covering said gap between the ends of said mechanism and said probe body member to prevent said gap for catching an end of the tube being inspected.

28. An improved probe for inspecting a tube of the type having a probe head assembly that includes a body member, a sensor holding mechanisms for resiliently holding a sensor with respect to said body member such that said sensor wipingly engages the inner walls of said tube when the probe head assembly is rotated and a gap is formed between the ends of said body member and said sensor holding mechanism, and a flexible cable that extends completely through said probe head assembly and which is secured to the body member of said assembly for rotating said assembly, wherein the improvement comprises:

a pair of centering devices, each of which includes an annular member mounted around the cable on either side of the probe head assembly for maintaining the axis of rotation of said cable in alignment with the center line of said tube, each annular member including a plurality of resilient finger members mounted around and extending away form the periphery of said annular member for engaging the inner walls of said tube and applying a centering force to said cable through said member, wherein each of said fingers is disposed in a plane that is orthogonal to the axis of rotation of said cable, but which is canted at an acute angle with respect to a line tangent to the portion of the annular member that it extends away form;

a button member resiliently mounted within said probe body member opposite from said sensor holding mechanisms for maintaining the axis of rotation of said probe head assembly in alignment with the center line of said tube;

a modular means for detachably mounting said sensor to said holding mechanism to facilitate replacing said sensor, at least one bumper member mounted onto said probe head assembly for covering said gap between the ends of said mechanism and said probe body member to prevent said gap from catching an end of a tube being inspected.

* * * * *